(12) United States Patent
Esmon et al.

(10) Patent No.: US 7,011,956 B1
(45) Date of Patent: Mar. 14, 2006

(54) THROMBOTIC EPISODE RISK ASSAYS USING OXIDIZED PHOSPHOLIPIDS

(75) Inventors: Naomi L. Esmon, Oklahoma City, OK (US); Omid Safa Jamilabadi, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 275 days.

(21) Appl. No.: 10/088,021

(22) PCT Filed: Sep. 26, 2000

(86) PCT No.: PCT/US00/26438
§ 371 (c)(1),
(2), (4) Date: Jul. 26, 2002

(87) PCT Pub. No.: WO01/23895
PCT Pub. Date: Apr. 5, 2001

Related U.S. Application Data
(60) Provisional application No. 60/156,564, filed on Sep. 28, 1999.

(51) Int. Cl.
C12Q 1/56 (2006.01)
G01N 33/86 (2006.01)
G01N 33/92 (2006.01)

(52) U.S. Cl. .............................. 435/13; 436/69; 436/71

(58) Field of Classification Search .................. 435/13; 436/69, 71
See application file for complete search history.

(56) References Cited

PUBLICATIONS

Aviram, et al., 1991. "Oxidized low–density lipoprotein reduces plama coagulation in–vitro," *Scand J Lab Invest* 51:17–21.
Barrowcliffe, et al. 1981. "Studies of phospholipid reagents used in coagulation I: general properties and their sensitivity to Factor VIII," *Thromb Haemostas* 46:629–633.
Barrowcliffe, et al. 1981. "Phospholipid reagents used in coagulation II: factors influencing their sensitivity to heparin," *Thromb Haemostas* 46:634–637.
Billy, et al. 1995. "Prothrombin contributes to the assembly of the factor Va–factor Xa complex at phosphatidylserine–containing phospholipid membranes," *J Biol Chem* 270:26883–26889.
Esmon, C.T. and Schwarz, H.P. 1995. "An update on clinical and basic aspects of the protein C anticoagulant pathway," *Trends Cardiovasc Med* 5:141–148.
Esmon, et al. 2000. "Antiphospholipid antibodies and the protein C pathway," *J Autoimmunity* 15:221–225.
Furie, B. and Furie, B.C. 1988. "The molecular basis of blood coagulation," *Cell* 53:505–518.
Gilbert, G.E. and Arena, A.A. 1995. "Phosphatidylethanolamine induces high affinity binding sites for factor VIII on membranes containing phosphatidyl–L–serine," *J Biol Chem* 270:18500–18505.
Horkko, et al. 1996. "Antiphospholipid antibodies are directed against epitopes of oxidized phospholipids," *J Clin Invest* 98:815–825.
Jain, S.K. 1985. "In vivo externalization of phosphatidylserine and phosphatidylethanolamine in the membrane bilayer and hypercoagulability by the lipid peroxidation of erythrocytes in rats," *J Clin Invest* 76:281–286.
Lesnik, et al. 1995. "Tissue factor pathway inhibitor activity associated with LDL is inactivated by cell– and copper–mediated oxidation," *Arteriosclerosis, Thrombosis and Vascular Biology* 15:1121–1130.
Malech, H.L. and Gallin, J.I. 1987. "Neutrophils in human diseases," *N Engl J Med* 317:687–694.
Mann, et al. 1988. "Cofactor proteins in the assembly and expression of blood clotting enzyme complexes," *Ann Rev Biochem* 57:915–956.
McCord, J.M. 1985. "Oxygen–derived free radicals in postischemic tissue injury," *N Engl J Med* 312:159–163.
Neuenschwander, et al. 1995. "Phosphatidylethanolamine augments factor VIIa–tissue factor activity: enhanceme of sensitivity to phosphatidylserine," *Biochemistry* 34:13988–13993.
Pei, et al. 1993. "Specific contribution of different phospholipid surfaces to the activation of prothrombin by the fully assembled prothrombinase," *J Biol Chem* 268:3226–3233.
Rauch, et al. 1986. "Human hybridoma lupus anticoagulants distinguish between lamellar and hexagonal phase lipid systems," *J Biol Chem* 261:9672–9677.
Smeets, et al. 1996. "Contribution of different phospholipid classes to the prothrombin converting capacity of sonicated lipid vesicles," *Thromb Res* 81:419–426.
Smirnov, M.D. and Esmon, C.T. 1994. "Phosphatidylethanolamine incorporation into vesicles selectively enhances factor Va inactivation by activated protein," *J Biol Chem* 269:816–819.
Smirnov, et al. 1995. "On the role of phosphatidylethanolamine in the inhibition of activated protein C activity by antiphospholipid antibodies," *J Clin Invest* 94:309–316.
Smirnov, et al. 1999. "The effect of membrane composition on the hemostatic balance," *Biochem* 38:3591–3598.

*Primary Examiner*—Sandra E. Saucier
(74) *Attorney, Agent, or Firm*—Eugenia S. Hansen; Conley Rose, P.C.

(57) ABSTRACT

An assay to assess thrombotic risk in which oxidized lipids comprising phospholipids are utilized as a membrane source in a clotting assay and the results compared to an assay in which unoxidized phospholipid is used as a membrane source in the presence and absence of activated protein C ("APC"). The assay can monitor for the presence of antibodies in the patient which interfere specifically with the anticoagulant function of APC in an oxidation dependent or independent manner. This can indicate the propensity of the patient to experience episodes of vein thrombosis or arterial thrombosis.

44 Claims, 1 Drawing Sheet

THROMBOTIC EPISODE RISK ASSAYS USING OXIDIZED PHOSPHOLIPIDS

This application claims the benefit of Provisional application No. 60/156,564 filed Sep. 28, 1999.

TECHNICAL FIELD OF THE INVENTION

This invention relates to the field of diagnostic blood clotting assays which are indicative of the risk of thrombotic episodes.

BACKGROUND OF THE INVENTION

It is well recognized that physiological blood coagulation requires the presence of membranes composed of negatively charged phospholipids. Zymogen activations occur rapidly when the enzyme, usually a vitamin K dependent protein, binds to a cofactor, usually a non-vitamin K dependent protein, to activate a substrate, usually a vitamin K dependent protein, reviewed in (Mann, K. G., Jenny R. J., and Krishnaswamy, S. 1988. "Cofactor proteins in the assembly and expression of blood clotting enzyme complexes," Ann. Rev. Biochem. 57:915–956; and Furie, B. and Furie, B. C. 1988. "The molecular basis of blood coagulation," Cell. 53:505–518). These reactions include those that are both procoagulant and those that are anticoagulant.

In addition to a net negative charge, the nature of the phospholipid head group appears to contribute to catalytic and binding efficiency. Phosphatidylserine (PS) is generally considered to be the most important phospholipid (Pei, G., Powers, D. D., and Lentz, B. R. 1993. "Specific contribution of different phospholipid surfaces to the activation of prothrombin by the fully assembled prothrombinase," J. Biol. Chem. 268:3226–3233; and Mann, K. G., Jenny R. J., and Krishnaswamy, S. 1988. Ann. Rev. Biochem. 57:915–956). It has been found that the presence of phosphatidylethanolamine (PE) or cardiolipin potently enhanced the rate of inactivation of factor Va by the activated protein C (APC) complex (Smirnov, M. D. and Esmon, C. T. 1994. "Phosphatidylethanolamine incorporation into vesicles selectively enhances factor Va inactivation by activated protein," C. J. Biol. Chem. 269:816–819). APC is a critical natural anticoagulant required for preventing lethal thrombosis. The inactivation of factors Va and VIIIa by the APC complex is crucial in the regulation of coagulation, as evidenced by the severe clinical problems which are observed if this reaction is compromised (Esmon, C. T. and Schwarz, H. P. 1995. "An update on clinical and basic aspects of the protein C anticoagulant pathway," Trends Cardiovasc. Med. 5:141–148). The presence of unsaturated fatty acids in the phospholipid vesicles also has been found to enhance the inactivation of factor Va (Smirnov, M. D., Ford, D. A., Esmon, C. T., and Esmon, N. L. 1999. "The effect of membrane composition on the hemostatic balance," Biochemistry 38:3591–3598). A role for PE in factor VIII binding (Gilbert, G. E. and Arena, A. A. 1995. "Phosphatidylethanolamine induces high affinity binding sites for factor VIII on membranes containing phosphatidyl-L-serine," J. Biol. Chem. 270:18500–18505), tissue factor-factor VIIa activation of factor X (Neuenschwander, P. F., Bianco-Fisher, E., Rezaie, A. R., and Morrissey, J. H. 1995. "Phosphatidylethanolamine augments factor VIIa-tissue factor activity: enhancement of sensitivity to phosphatidylserine," Biochemistry 34:13988–13993) and prothrombin activation (Smeets, E. F., Comfurius, P., Bevers, E. M., and Zwaal, R. F. A. 1996. "Contribution of different phospholipid classes to the prothrombin converting capacity of sonicated lipid vesicles," Thromb. Res. 81:419–426; and Billy, D., Willems, G. M., Hemker, H. C., and Lindhout, T. 1995. "Prothrombin contributes to the assembly of the factor Va-factor Xa complex at phosphatidylserine-containing phospholipid membranes," J. Biol. Chem. 270:26883–26889) has also been reported. In those latter studies, the PE effects were different both qualitatively and quantitatively from those on the APC complex (Sec (Smirnov, M. D., Ford, D. A., Esmon, C. T., and Esmon, N. L. 1999. Biochemistry 38:3591–3598) for discussion).

One group of patients who are at increased risk for thrombotic diseases are those who have lupus anticoagulants, which are antibodies which bind to anionic phospholipids used in clotting assays based on the PTT (partial thromboplastin time) or APTT (activated partial thromboplastin time) techniques. See The Merck Manual (16th Ed. 1992) at 1225; J. E. Ansell, Handbook of Hemostasis and Thrombosis (Little, Brown & Co., Boston) at 19 (1986). Typical PTT test results for patients having the lupus anticoagulant are a prolonged clotting time that fails to correct with a 1:1 mixture of the patient's and normal plasma, a normal or minimally prolonged PT (prothrombin time), and a nonspecific depression of those clotting factors measured by a PTT technique (Factors XII, XI, X and VIII). The lupus anticoagulant antibodies may also react with cardiolipin which can interfere with assays utilizing cardiolipin as a reagent. See The Merck Manual, supra. Anti-cardiolipin or anti-phosphatidylethanolamine antibodies can cross react with each other, but not interact with sufficient affinity to procoagulant phospholipids to be anticoagulants. Because of the specificity of the APC complex for phospholipids, such antibodies would selectively inhibit APC anticoagulant activity without influencing the coagulation tests performed in the absence of APC which are used to diagnose the presence of a "lupus anticoagulant."

Despite interference of the lupus anticoagulant antibodies with procoagulant phospholipid in clotting tests in vitro, persons with the antibodies have been reported to have an increased risk for thrombosis, either venous or arterial. Further, repeated spontaneous abortions in the first trimester of pregnancy have also been reported. Id. Patients have been treated with long term anticoagulant therapy to reduce the possibility of thrombosis, but no adequate technique has been developed for monitoring the effectiveness of such therapy. It should also be noted that other patients, who do not necessarily test positively for the lupus anticoagulant, may also be at risk for thrombotic disease due to the presence of antibodies not detected by current clotting tests. Further, not all persons who have the lupus anticoagulant or other risk factors have an identical propensity for thrombosis.

In order to attempt to identify patients at risk for thrombosis, standard clotting tests have been performed on patient plasma. Because anticoagulant therapy carries significant risk in some patients, it is highly desirable to determine whether patients are likely to benefit from such therapy. Additional testing has been suggested as described above where PTT and/or PT test results do not appear to be normal, such as repeating the test with added normal plasma or further addition of excess phospholipid. Previously, a technique was developed to differentiate among lupus patients and among others which patients have the highest propensity to have a thrombotic incident. This method was disclosed and claimed in U.S. Pat. No. 5,472,852, discussed infra.

Previously, we observed that at least a subpopulation of lupus anticoagulants can inhibit the APC anticoagulant activity more effectively than prothrombin activation (Smirnov, M. D., Triplett, D. T., Comp, P. C., Esmon, N. L., and Esmon, C. T. 1995. "On the role of phosphatidylethanolamine in the inhibition of activated protein C activity by antiphospholipid antibodies," J. Clin. Invest. 94:309–316). This difference is dramatically augmented by the presence of PE in the membrane bilayer (Smirnov, M. D., Triplett, D. T., Comp, P. C., Esmon, N. L., and Esmon, C. T. 1995. J. Clin. Invest. 95:309–316; and Rauch, J., Tannenbaum, M., Tannenbaum, H., Ramelson, H., Cullis, P. R., Tilcock, C. P. S., Hope, M. J., and Janoff, A. S. 1986. "Human hybridoma lupus anticoagulants distinguish between lamellar and hexagonal phase lipid systems," J. Biol. Chem. 261: 9672–9677).

In U.S. Pat. No. 5,472,852, entitled "Assay For Detection of Selective Protein C Inhibition by Patients" a method for determining the propensity of a patient to have a thrombotic incident was disclosed. A membrane source was utilized in the assay comprising an effective amount of phosphatidylethanolamine (PE) and an effective amount of phosphatidylserine (PS). Preferably, 10 to 50% PE and 5 to 50% of PS was utilized in the assay. Phosphatidylcholine (PC) could be used in the assay to make up any remaining percentage. In the assay disclosed and claimed in the '852 patent, patient and control plasma is assayed in the presence and absence of exogenous activated protein C (APC). By comparing the clotting times of samples with and without exogenous APC and optimal phospholipids, the risk of thrombotic disease can be assessed.

During the process of clot formation, leukocytes are recruited into the growing thrombus and become activated. These activated leukocytes have been reported to release potent oxidizing agents like hydrogen peroxide and superoxide, substances known to oxidize phospholipids. Malech, H. L. and Gallin, J. I. 1987. "Neutrophils in human diseases," N. Engl. J. Med. 317:687–694; McCord, J. M. 1985. "Oxygen-derived free radicals in postischemic tissue injury," N. Engl. J. Med. 312:159–163.

Although it has been established that phospholipids have an important role in coagulation, and coagulation assays such as discussed above, and some reports on specific parameters of the phospholipids have been reported as discussed above, there is a continuing need to improve assays for determining the risk of thrombotic disease by improving reagents used in such assays. In addition, although reports as to release of oxidizing agents from leukocytes have inferred that membrane oxidation may be involved in thrombosis, there has been no report or prediction of a differential effect of oxidation of lipids on APC activity.

It has now been found that oxidized phospholipids selectively enhance the anticoagulant properties of APC, with little impact on the clot-promoting reactions. It has also been found that a subset of antiphospholipid antibodies selectively eliminate the oxidized lipid enhancement. An assay is herein disclosed which is useful for assessing the risk of thrombotic episodes by utilizing oxidized and nonoxidized phospholipids as separate reagents. The sample is tested for clotting by using each of the reagents in a parallel assay. The results are compared to those obtained with normal plasma to assess whether the sample plasma may contain indicators of thrombotic disease.

DETAILED DESCRIPTION OF THE INVENTION

Figure 1:
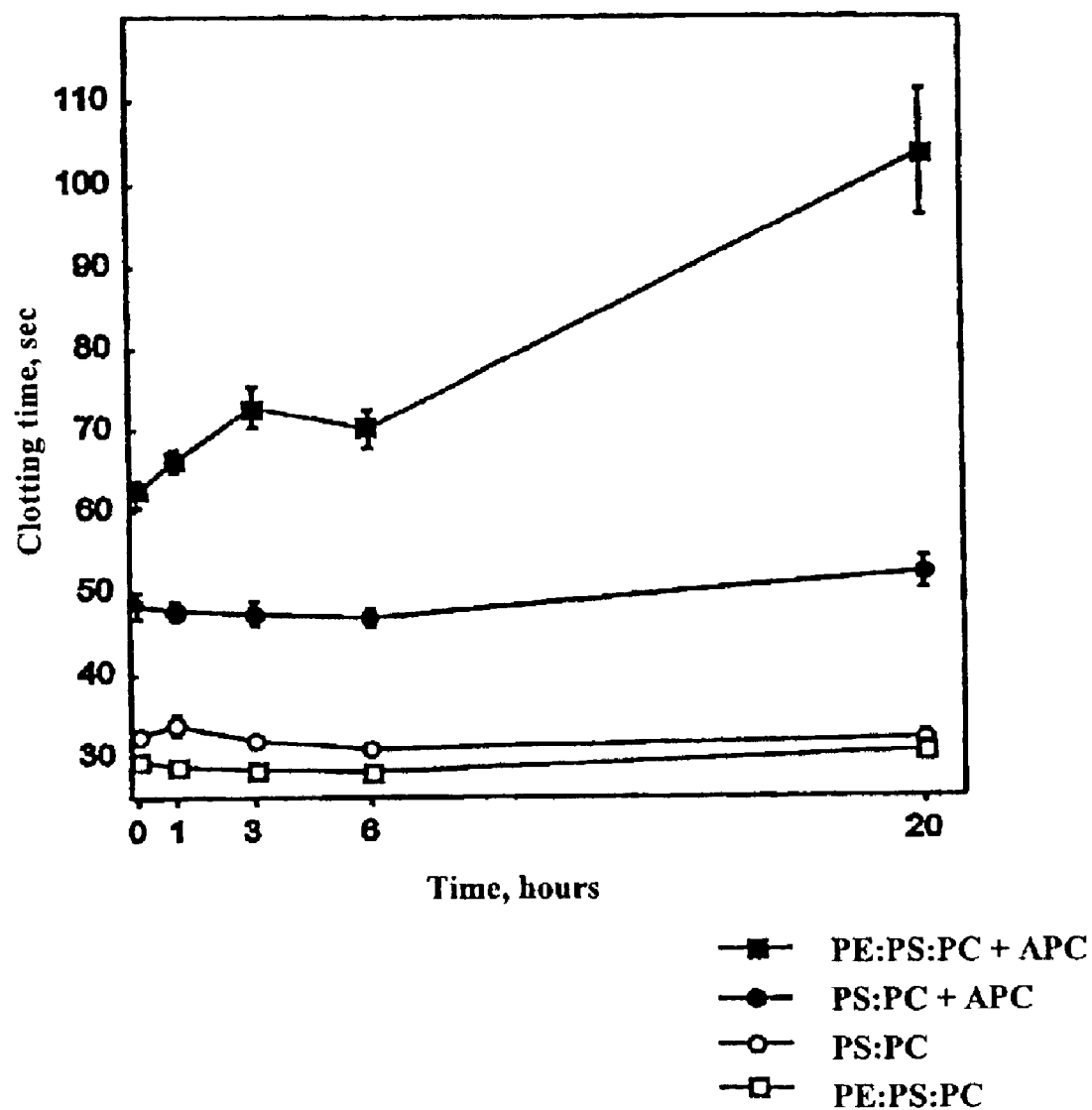
FIG. 1 is a graph depicting the effect of phospholipid oxidation on coagulation assays in the presence or absence of APC determined as a function of time of oxidation of the phospholipid. Assays were run on the following: PE:PS:PC with APC (closed square) and without APC (open square), and PS:PC with APC (closed circle) and without APC (open circle). Oxidation of PE containing vesicles dramatically enhanced the anticoagulant activity of APC.

We have now found that lipid oxidation is a mechanism for making the thrombus less thrombogenic by enhancing the anticoagulant activity of the activated protein C ("APC") complex. As a result, patients having antibodies targeted to oxidized phospholipids are likely unable to adequately prevent thrombus extension and are concomitantly more prone to deep vein thrombosis and arterial thrombosis. The specificity of these antibodies prevent the evolution of the thrombus from clot-promoting to clot-inhibiting.

Recent data has indicated that many of the antibodies identified by current assays are either partially or entirely targeted toward oxidized forms of either the lipid or protein antigen (see, for example, Horkko, S., Miller, E., Dudi, E., Reaven, P., Curtiss, L. K., Zvaifler, N. J., Terkeltaub, R., Pierangeli, S. S., Branch, D. W., Paliski, W. et al. 1996. "Antiphospholipid antibodies are directed against epitopes of oxidized phospholipids. Recognition of cardiolipin by monoclonal antibodies to epitopes of oxidized low density lipoprotein," J. Clin. Invest. 98:815–825). Surprisingly, it has now been found that oxidized phospholipids, that include phosphatidylethanolamine (PE), further enhances the activity of APC in the factor Va inactivation complex. In addition, the ability of at least a class of lupus anticoagulant or anti-phospholipid antibodies to inhibit APC activity is augmented by the presence of oxidized phospholipid. Patient plasma may be screened by assaying it in a one stage assay in the presence and absence of activated protein C, according to the methodology described in U.S. Pat. No. 5,472,852 which is herein incorporated by reference. The method of the '852 patent can be modified by using a membrane source comprising an effective amount of oxidized phospholipid which includes PE.

In place of Factor X-activating enzyme from Russell's viper venom, any activator of Factor X (or Factor $X_a$ itself) may be utilized. Contact activation of coagulation. Tissue Factor, Factor $IX_a$, or $XI_a$ may be used, as described in the '852 patent.

Additional procedures may be helpful to the assay of the invention or interpretation of data derived therefrom. It may be desirable to determine baseline clotting values for patient samples in the absence of APC, as set forth in Example 2, in order to better assess characteristics of particular samples which will be tested in the assay in the presence of APC, with oxidized phospholipid reagent as compared to non-oxidized phospholipid reagent. Another procedure which may be desirable is assaying cloning time of a purified subportion or fraction of the patient plasma which is the immunoglobulin. A procedure for purifying immunoglobulin from patient plasma or serum is provided in Example 3, and there are other purification procedures known to the art that could be employed as well. Another additional procedure which can be used, when using either patient plasma or patient purified immunoglobulin as a test sample, is diluting the test sample in known normal plasma. An appropriate dilution to use in the assay of the present invention may be determined by standard techniques such as preparing serial dilutions of the test sample, conducting clotting assays set forth herein on the various dilutions, and determining which dilutions provide desirable assay conditions such as time of clotting and permit the operator to determine differences which may occur, so that such differences are not masked by possible high concentrations of various factors in the sample or unusually low concentrations (as may occur from a disease or course of medication). In addition, samples which are too dilute may not have detectable differences in the assay. A preferred dilution of patient plasma in normal plasma has been found to be about one part patient plasma to three parts normal plasma—an approximate 1:4 dilution. In case of immunoglobulin patient samples, a concentration of about 0.6 mg/ml has been found to be most preferred.

In the assay of the present invention, a reagent comprising appropriate oxidized lipids is utilized. Appropriate oxidized lipids comprise a quantity of PE, preferably in combination with other phospholipids, and most preferably in combination with phosphatidylserine (PS). In another embodiment, the reagent used in the assay of the present invention comprises PE and phosphatidylcholine (PC). Most preferably, a reagent useful in the present invention comprises PE, PS and PC. Preferably, a natural lipid source is utilized to make the reagent, but it is contemplated that synthetic lipids could also be utilized if vesicles made therefrom exhibit sufficiently similar behavior to vesicles made from natural-source lipids in assays measuring the clotting time of normal plasma.

Other lipid reagents with different compositions of phospholipids may be made in a similar manner by varying the proportions of phospholipids used. Preferably, the lipid reagents are used of the composition described in U.S. Pat. No. 5,472,852. Specifically, a phospholipid component which comprises an effective amount of PE to provide a differential, detectable effect between normal (control) plasma and plasma from patients having a propensity for thrombotic episodes and an effective amount of PS to complement said PE in a clotting assay is employed. Preferably, the phospholipid component comprises from about 10% to about 50% PE, from about 5% to about 50.% PS and the remainder PC or any phospholipid which is zwitterionic and has no net charge at neutral pH. Preferably, the PS component is from about 5% to about 25% of the phospholipid component. In a most preferred embodiment, the phospholipid component of the membrane source comprises about 40% PE, about 20% PS and about 40% PC by weight of the phospholipid component.

The phospholipids utilized to make the lipid reagent should be substantially non-oxidized prior to use, and precautions should be taken during preparation to maintain the phospholipids in a non-oxidized state until it is desired to make an oxidized reagent. The choice of the commercial source of the phospholipids has been found to be one variable in the degree of oxidation present in the non-oxidized controls. For example, we have found that those purchased from Avanti Polar Lipids, Inc. are much less oxidized than those purchased from other sources, based on both supplier statements and the enhancement in APC activity observed after copper-catalyzed oxidation. There are several methods available to test phospholipids for oxidation. One method is to observe the phospholipids with the unaided eye to determine if the phospholipids appear to be discolored. Oxidized phospholipids appear off-color or yellow in comparison to non-oxidized phospholipids. This is especially true of PE and PS. In addition, a simple spectrophotometric test is available. The ratio of the absorption bands at 233 and 215 nanometers in the UV-spectrum can be measured according to the procedure of Klein, R. A., Biochim Biophys Acta, 210:486 (1970). A ratio of 0.02 corresponds to about 0.1% oxidation products according to the Klein method. For the lipid reagent useful in the invention, it is desirable to utilize substantially non-oxidized lipids which when used in a reagent and tested against results obtained when oxidized lipids are used as reagent, will demonstrate a significant difference in the clotting time of normal plasma, in the presence of APC, as seen in Table I.

Prevention of oxidation can be accomplished by maintaining the phospholipids under argon or nitrogen gas. Therefore, diluting the phospholipid into extensively degassed buffer, preferably a buffer pretreated with Chelex 100 resin (Biorad), vortexing under nitrogen or argon is a method of preserving lipids in a non-oxidized state.

EXAMPLE 1

Method Of Preparing Non-Oxidized And Oxidized Phospholipid Reagents

A reagent useful in the assay of the present invention was prepared comprising 40% PE, 20% PS and 40% PC. The individual phospholipids derived from bovine brain (and therefore comprised of naturally-occurring fatty acids) were obtained from Avanti Polar Lipids, Inc. They were tested using the Klein spectrophotometric assay and found to be less than 1% oxidized. The lipids were mixed in the weight proportions indicated, dried under argon and lyophilized 3 hours to remove organic solvents. They were then reconstituted under argon, suspended by vortex in 0.15 M NaCl, 10 mM HEPES, pH 7.5 or 0.15 M NaCl, 20 mM Tris HCl, pH 7.4 to 5 mg/ml total lipid. Buffers were treated with Chelex 100 resin (BioRad) and saturated with argon before use. Other reagents with different compositions of phospholipids may be made in a similar manner by varying the proportions of phospholipids used.

Liposomes were prepared by extrusion through a 100 nm polycarbonate filter (Nucleopore). The non-oxidized liposomes so prepared can be used immediately or stored. The non-oxidized liposomes may be stored under argon until needed for the assay or until oxidation is desired, for up to about three days at room temperature. Because a quantity of non-oxidized liposomes is needed for comparative purposes in the assay of the invention, it may be desirable to add a stabilizing agent effective for preventing oxidation to a quantity of non-oxidized liposomes which will be used in the assay in non-oxidized form. Such stabilizing agents include EDTA and antioxidants such as BHT or equivalents thereof. In a specific example, 1 mM EDTA was added to a preparation made in accordance with the method provided above to preserve liposomes in a non-oxidized state. For non-oxidized liposomes which are to be further processed to oxidized liposomes using the methods given below, it is undesirable to add stabilizing agents.

Oxidized liposomes for use in the assay of the present invention may be made by allowing exposure of non-oxidized liposomes to air or by employing an oxidizing reaction. It is preferred that an oxidizing reaction be used so that a degree of control may be applied to the process. For oxidation, 1 $\mu$l of 10 mM $CuSO_4$ was added to 1 ml of liposomes (200 $\mu$g/ml) to yield 10 $\mu$M $CuSO_4$ in a glass tube. The copper ion acts as a catalyst for air oxidation of the phospholipids. The suspension was then vortexed at 37° C. to introduce air into the solution. Other methods of oxidation, such as those discussed in references (Chatterjee, S. N. and Agarwal, S. 1988. "Liposomes as membrane model for study of lipid peroxidation," Free Radical Biology and Medicine 4:51–72; and Goni, F. M. and Alonso, A. 1989. "Studies of phospholipid peroxidation in liposomes," In CRC Handbook of Free Radicals and Antioxidants in Biomedicine, J. Miquel, Quintanilha, A. T., and Weber, H., editors. CRC Press, Inc., Boca Raton, Fla. 103–122), may also be used as long as it is controlled so that the vesicles do not disintegrate, as determined by empirical observation. Oxidation by air alone can be used, but it is preferred to generate the oxidized lipids utilizing an oxidizing reaction exemplified above. In any of the methods, the reaction can be blocked as desired by adding a chelating agent effective for blocking the catalyst or an antioxidant such as BHT. The suitability of the oxidized lipids may be assessed by a preliminary titration test comprising a clotting assay. In the environment and using conditions known to one skilled in the art of clotting assay, one can determine whether prolonged clotting occurs in the presence of APC in the preliminary titration test as compared to clotting assays with non-oxidized lipids.

EXAMPLE 2

Determination of Baseline Clotting Values in The Absence of APC And Comparison To Values In The Presence of APC Coagulation assays were performed as one stage clotting assays using the ST4 coagulation instrument (Diagnostica Stago, Parsippany, NJ). For assays in which APC and/or immunoglobulin (normal or patient sample) were omitted, volumes were made up with buffer (0.1 M NaCl, 0.02 M Tris-HCl, pH 7.5, 1 mg/ml gelatin).

The effect of lipid oxidation on coagulation assays in the presence or absence of APC was determined as a function of time of oxidation of the phospholipid (FIG. 1). Pooled normal plasma (50 μl) was placed in the reaction vessels and the following reagents added to the final concentrations indicated in parentheses: Factor X-activating enzyme from Russell's viper venom (prepared as per C. T. Esmon, Dissertation, Washington University, St. Louis, 1973) or obtained from American Diagnostica, Greenwich, CN) (0.1–0.15 nM, sufficient to yield a 30 sec clotting time in the absence of APC); Phospholipid (10 μg/ml); APC (0.2 μg/ml); buffer to bring the final volume to 200 μl. After 1 min incubation at 37° C., clotting was initiated with $CaCl_2$ (6.25 nM).

Neither the presence of PE nor 20 hours of copper catalyzed lipid oxidation had a significant effect on the clotting assay in the absence of APC. Oxidation of vesicles containing only PS and PC did not enhance the ability of the vesicles to support APC anticoagulant activity. Oxidation of PE containing vesicles dramatically enhanced the anticoagulant activity of APC.

Baseline clotting values for plasma test samples as compared to known normal plasma can be obtained by measuring clotting time in the absence of APC, using oxidized or non-oxidized lipids. This determination will account for the possible contribution of strong lupus anticoagulant activity or other unknown components in the patient sample to the prolongation of clotting time. If one determines that the clotting time of the patient sample in the absence of APC is several (e.g., greater than 5 seconds) seconds longer than the clotting time of normal plasma in the absence of APC, then it will be expected that the clotting time of the patient sample in the presence of APC, whether or not the lipid source is oxidized, will be much longer than that of normal plasma.

In addition, the methodology of Example 2 may be modified by utilizing one of the additional measures discussed, supra, such as dilution of the patient sample in normal plasma prior to assaying or purification of immunoglobulin from said sample as discussed in Example 3.

EXAMPLE 3

Evaluation of Normal Plasma-Derived IgG Compared to IgG from Plasma of Patents with Diagnosed Clotting Disorders Patients used in this study are described in Table I. Patients 1–7 were evaluated as follows. Double centrifuged citrated plasma was used for all coagulation assays and prepared according to the method of Sletnes, K. E., Gravem, K., and Wisloff, F. 1992. "Preparation of plasma for the detection of lupus anticoagulants and antiphospholipid antibodies." Thromb. Res. 66;43–53. The presence or apparent absence of lupus anticoagulant was determined by a prolonged clotting time with a commercial PTT reagent ($Staclot^R$ LA, Diagnostica Stago) in a 50:50 mixture of test plasma and normal plasma. Plasma with clotting times exceeding the 95th percentile of a previously established control population underwent additional testing. The diagnosis was confirmed by normalization or significant correction of the clotting time (≧8 seconds) in the presence of hexagonal (II) phase phospholipid. Anti-cardiolipin IgG and IgM were tested by commercial ELISA methods on serum samples (Quanta Lite aCL IgG, IgM, Inova Diagnostics, San Diego, CA). Antibodies to prothrombin, protein S and P2-glycoprotein I were analyzed by ELISA as previously described (Safa, O., Crippa, L., Della, V. P., Sabbadini, M. G., Vigano, D. S., and D'Angelo, A. 1999. "IgG reactivity to phospholipid-bound beta(2)-glycoprotein I is the main determinant of the fraction of lupus anticoagulant activity quenched by addition of hexagonal (II) phase phospholipid in patients with the clinical suspicion of antiphospholipid-antibody syndrome." Haematologica 84:829–838).

Patients 8–13 were evaluated for lupus anticoagulant activity using either previous reports from medical records (in the case of patients who were anticoagulated since registration) or a commercially available kit for the dilute Russell's viper venom assay (American Diagnostica, DVVT #810 and DVV Confirm #815). Anti-cardiolipin IgG and antibodies to prothrombin, protein S, β2-glycoprotein I and Annexin V were determined by standard ELISA techniques as described previously for P2-glycoprotein 1 (Merrill, J. T., Shen, C., Lahita, R. G., and Mongee, A. B. 1997. "High prevalence of antiphospholipid antibodies in patients taking procainamide." J. Rheum. 24:1083–1088).

Previously, we showed that plasma or immunoglobulin derived from at least a subset of lupus patients could inhibit APC function selectively in a phosphatidylethanolamine dependent manner. Smirnov, M. D., Triplett, D. T., Comp, P. C., Esmon, N. L., and Esmon, C. T. 1995. "On the role of phosphatidylethanolamine in the inhibition of activated protein C activity by antiphospholipid anitbodies." J. Clin. Invest. 95:309–316; and Smirnov, M. D., Ford, D. A., Esmon, C. T., and Esmon, N. L. 1999. "The effect of membrane composition on the hemostatic balance," Biochemistry 38:3591–3598). Although normal precautions against oxidation were taken, including storage under argon and usage within one week of liposome preparation, the oxidation state of the phospholipids used in those studies was not specifically known.

To test whether the use of oxidized lipids affect the clotting time, IgG from a selection of lupus and thrombosis patients was tested for activity against APC on oxidized vs non-oxidized liposomes.

Immunoglobulin (IgG) was purified from thrombotic patients by standard procedures. Plasma or serum was precipitated with 50% NH$_4$SO$_4$. The precipitate was resuspended and dialyzed vs 0.1 M NaCl, 0.02 Tris-HCl, pH 7.5. This material was then applied to a protein G column (Amersham-Pharmacia), washed with buffer and eluted with 0.1 M glycine, pH 2.5. The eluate was immediately neutralized with 1 M Tris-HCl, pH 9 and dialyzed vs buffer. Immunoglobulin was added to the clotting assays to a final concentration of 0.6 mg/ml.

The results of these assays are given in Table I. As performed, this assay is relatively insensitive to lupus anticoagulant activity ($\leq$5 sec prolongation), which permits simplification of the data presented, and only the elongation of clotting time in the presence of APC is shown. Patients 1–7 originated from a coagulation service but were also selected as lupus anticoagulant positive. Patients 8–13 with systemic lupus erythematosis originated from a rheumatology clinic. In both groups where thrombosis has occurred, immunoglobulin exhibiting oxidation specific inhibition of APC activity is seen (Patients 1, 2, 4, 10). These immunoglobulins had little effect on APC anticoagulant activity on non-oxidized phospholipid. Patients in each group (Patients # 6, 7 and 12) showed decreased activity on both lipid preparations. In the case of Patient #7 and especially Patient #12, differential activity on oxidized vs non-oxidized lipid was essentially maintained.

Therefore, testing a patient plasma sample in an assay in the presence of APC, and obtaining a first clotting time by using an oxidized lipid reagent and a second clotting time by using an unoxidized lipid reagent provides a method to subclassify antibody functional activity in patient plasma. If the first clotting time is essentially the same as the second clotting time, one can predict that the patient sample likely contains antibodies which block the function of oxidized lipids to a greater extent than unoxidized lipids. This data may be useful for predicting the propensity for thrombotic disease or recurrence of thrombotic episodes.

If the plasma is normal, or does not contain such antibodies, one would expect a longer clotting time with the use of an oxidized phospholipid reagent as compared to a non-oxidized phospholipid reagent. (See Table 1, Norm 1 and Norm 2).

TABLE I

Characterization of Patients

| Patient #[1] | Sex | History[2] | LA[3] | ACA[4] | Other Antibody Reactivities[5] | Clotting Time (sec) with Oxidized Phospholipids[6] | Clotting Time (sec) with Non-oxidized Phospholipids[7] |
|---|---|---|---|---|---|---|---|
| 1 | F | DVT; EM | + | +++ (IgG) | PrS, β2 | 34.1 | 33.7 |
| 2 | F | DVT; 3 miscarriages | + | +++ (IgG) | Pt, PrS, β2 | 31.2 | 34.0 |
| 3 | F | DVT; lupus-like syndrome | + | — | Pt | 54.4 | 35.6 |
| 4 | M | MI; ischemic stroke | + | +++ (IgG) | Pt, β2 | 35.2 | 34.0 |
| 5 | F | polyarthritis | + | + (IgM) +/− (IgG) | — Pr, PrS, β2(+/−) | 56.9 | 27.1 |
| 6 | F | lupus-like demyelinating syndrome | + | +++ (IgG) | Pt, β2 | 25.0 | 28.7 |
| 7 | F | DVT; SLE | + | + (IgG) | Pt, β2 | 36.0 | 27.0 |
| 8 | F | SLE | + | +++ (IgG) | Pt | 82.0 | 37.1 |
| 9 | F | SLE; DVT; 2 fetal losses | − | ++ (IgG) | Pt, PrS | 90.7 | 39.6 |
| 10 | F | SLE; 2 DVTs; 3 fetal losses | + | — | Pt, PrS, β2 | 41.5 | 39.0 |
| 11 | F | SLE; necrotizing vasculitis | + | — | PrS, β2 (+/−) | 90.3 | 41.5 |
| 12 | F | SLE; CVA; preeclampsia; phlebitis | + | ++ (IgG) | Pt, AnV | 56.8 | 30.1 |
| 13 | F | 4 fetal losses | − | + (IgG) | Pt, PrS | 92.8 | 39.8 |
| Norm1 | | | | | | 66.7 | 32.6 |
| Norm2 | | | | | | 99.0 | 44.0 |

[1]Norm1 = normal control patients #1–7; Norm2 = normal control for patients #8–13
[2]DVT = deep vein thrombosis; EM = pulmonary embolism; M1 = myocardial infarction; SLE = systemic lupus erythematosis; and CVA = cerebral vascular accident.
[3]LA = lupus anticoagulant; patients #1–7 based on Staclot ® LA assay (available from Diagnostica Stago, Inc.); patients #8–13 based on dilute Russell's Viper Venom Time (dRVVT) assay for American Diagnostica.
[4]ACA = anti-cardiolipin anti-body; IgM was not measured in patients #8–13.
[5]All samples were tested in ELISA for reactivity to prothrombin (Pt), protein S (PrS) and β$_2$-glycoprotein 1 (β2). Only patients #8–13 were tested against annexin V (AnV).
[6]Assay results reported as clotting time measured with oxidized liposomes in the presence of APC minus the clotting time with oxidized liposomes in the absence of APC.
[7]Assay results reported as clotting time measured with non-oxidized liposomes in the presence of APC minus the clotting time with non-oxidized liposomes in the absence of APC

We claim:

1. In a coagulation assay for determining the propensity of patient risk for thrombotic disease wherein a phospholipid comprising phosphatidylethanolamine and phosphatidylserine is employed as a reagent and activated protein C is utilized in the assay, the improvement comprising conducting said assay with an oxidized phospholipid reagent to obtain a first result and a non-oxidized phospholipid reagent otherwise identical in composition to said oxidized phospholipid reagent to obtain a second result, and comparing said first and second result, and if said first result is prolonged in comparison to said second result, concluding that said patient is likely normal but if said first result is essentially the same as said second result, concluding that said patient likely has antibodies which block the function of oxidized phospholipids to a greater extent than unoxidized phospholipids and that said patient risk for thrombotic disease is higher than that observed for normal patients.

2. An assay to determine the presence of blocking antibodies in a patient plasma sample, which blocking antibodies selectively block the enhanced anticoagulant effect of activated protein C in the presence of oxidized phospholipids, comprising:

(a) conducting a clotting assay by obtaining a first aliquot of said sample, providing activated protein C, providing an oxidized phospholipid reagent comprising phosphatidylethanolamine and phosphatidylserine, initiating clotting and measuring the time of clotting to obtain a first clotting time;

(b) simultaneously or thereafter conducting a clotting assay by obtaining a second aliquot of said sample, providing activated protein C, providing an unoxidized phospholipid reagent otherwise identical in composition to said oxidized phospholipid reagent in step (a), initiating clotting and measuring the time of clotting to obtain a second clotting time;

(c) comparing said first clotting time with said second clotting time and determining that the patient sample likely contains blocking antibodies which block the action of activated protein C on oxidized lipids to a greater extent than on unoxidized lipids if said first clotting time is not prolonged or is essentially the same as compared to said second clotting time.

3. The assay of claim 2, further comprising obtaining baseline clotting values, said baseline clotting values obtained by measuring the clotting time of a third aliquot of said sample in the presence of an oxidized phospholipid reagent comprising phosphatidylethanolamine and phosphatidylserine, but without addition of activated protein C, and obtaining a third clotting time baseline value, and measuring the clotting time of a fourth aliquot of said sample in the presence of a non-oxidized phospholipid reagent, otherwise identical in composition to said oxidized phospholipid reagent but without addition of activated protein C, and obtaining a fourth clotting time baseline value, thereby determining if a given patient sample exhibits extended clotting time in the absence of activated protein C in comparison with a normal plasma sample, and concluding that said patient sample may have other components which may account for a prolonged clotting time when clotting time is tested in the presence of activated protein C according to steps (a) and (b).

4. The assay of claim 2 or 3, wherein each of said phospholipid reagents further comprise phosphatidylcholine.

5. The assay of claim 2 or 3, wherein each of said phospholipid reagents comprise 40% phosphatidylethanolamine, 20% phosphatidylserine and 40% phosphatidylcholine.

6. The assay of claim 2, further comprising the steps of:
(d) conducting a third clotting assay by obtaining a first aliquot of a normal patient plasma, providing activated protein C, providing said oxidized phospholipid reagent, initiating clotting and measuring the time of clotting to obtain a third clotting time;
(e) conducting a fourth clotting assay by obtaining a second aliquot of sad normal patient plasma, providing activated protein C, providing said non-oxidized phospholipid reagent, initiating clotting and measuring the time of clotting to obtain a fourth clotting time; and
(f) concluding that if the first clotting time is not as prolonged as the second clotting time, taking into account how much said third clotting time is prolonged over said fourth clotting time, then said patient sample likely contains said blocking antibodies.

7. The assay of claim 2 or 3, wherein said phospholipid reagent comprises an effective amount of phosphatidylethanolamine to provide a differential, detectable effect between normal (control) plasma and plasma from patients having a propensity for thrombotic episodes and an effective amount of phosphatidylserine to complement said phosphatidylethanolamine in said clotting assay.

8. The assay of claim 2 or 3, wherein said phospholipid reagent comprises from about 10 to about 50% phosphatidylethanolamine and from about 5 to about 50% phosphatidylserine.

9. The assay of claim 8, wherein said phospholipid reagent further comprises a phospholipid selected from the group consisting of phosphatidyl choline and zwitterionic phospholipids which have no net charge at neutral pH.

10. The assay of claim 2 or 3, wherein said phospholipid reagent comprises phosphatidylserine in an amount from about 5 to about 25%.

11. The assay of claim 10, wherein said phospholipid reagent further comprises a phospholipid selected from the group consisting of phosphatidyl choline and zwitterionic phospholipids which have no net charge at neutral pH.

12. The assay of claim 2 or 3, wherein said phospholipid reagent further comprises a phospholipid selected from the group consisting of phosphatidyl choline and zwitterionic phospholipids which have no net charge at neutral pH.

13. The assay of claim 2 or 3, wherein said phospholipid reagent comprises about 40% phosphatidylethanolamine, about 20% phosphatidylserine and the remainder a phospholipid selected from the group consisting of phosphatidyl choline and zwitterionic phospholipids which have no net charge at neutral pH.

14. The assay of claim 2 or 3, wherein clotting is initiated by addition of an initiator selected from the group consisting of Factor X-activating enzyme and Factor $X_a$.

15. The assay of claim 2 or 3, wherein a patient immunoglobulin fraction is obtained from said patient's serum or from said plasma sample, and said immunoglobulin fraction is utilized for said clotting time measurements.

16. The assay of claim 15, further comprising diluting said immunoglobulin fraction in an appropriate amount of normal plasma prior to measuring said first and second clotting times.

17. The assay of claim 16, wherein said appropriate amount of normal plasma is about three parts for each one part of patient sample.

18. The assay of claim 17, wherein said appropriate amount of normal plasma is sufficient to make said immunoglobulin fraction concentration about 0.6 mg/ml in said assay.

19. The assay of claim 2 or 3, further comprising diluting said plasma sample in an appropriate amount of normal plasma prior to measuring said first and second clotting times.

20. The assay of claim 19, wherein said appropriate amount of normal plasma is about three parts for each one part of patient plasma sample.

21. An assay to determine the propensity of a patient to have a thrombotic episode by measuring a first clotting time of a plasma sample taken from said patient in the presence of activated protein C and an oxidized phospholipid reagent comprising phosphatidylethanolamine and phosphatidylserine, measuring a second clotting time of a plasma sample taken from said patient in the presence of activated protein C and an unoxidized phospholipid reagent otherwise identical in composition to said oxidized phospholipid reagents and analyzing the results, determining that said patient has a propensity for a thrombotic episode if said first clotting time is not prolonged as compared to said second clotting time.

22. The assay of claim 21, wherein a patient immunoglobulin fraction is obtained from said patient's serum or from said plasma sample, and said immunoglobulin fraction is utilized for said clotting time measurements.

23. The assay of claim 22 further comprising diluting said immunoglobulin fraction in an appropriate amount of normal plasma prior to measuring said first and second clotting times.

24. The assay of claim 23, wherein said appropriate amount of normal plasma is sufficient to make said immunoglobulin fraction concentration about 0.6 mg/ml in said assay.

25. The assay of claim 24, wherein clotting is initiated by addition of an initiator selected from the group consisting of Factor X-activating enzyme and Factor $X_a$.

26. The assay of claim 23 wherein said appropriate amount of normal plasma is about three parts for each one part of patient sample.

27. The assay of claim 21, further comprising diluting said plasma sample in an appropriate amount of normal plasma prior to measuring said first and second clotting times.

28. The assay of claim 27, wherein said appropriate amount of normal plasma is about three parts for each one part of patient plasma sample.

29. The assay of claim 28 or 24 wherein each of said phospholipid reagents further comprise phosphatidylcholine.

30. The assay of claim 28 or 24, wherein each of said phospholipid reagents comprise 40% phosphatidylethanolamine, 20% phosphatidylserine and 40% phosphatidylcholine.

31. The assay of claim 28, wherein clotting is initiated by addition of an initiator selected from the group consisting of Factor X-activating enzyme and Factor $X_a$.

32. The assay of claim 27 wherein each of said phospholipid reagents further comprise phosphatidylcholine.

33. The assay of claim 27, wherein clotting is initiated by addition of an initiator selected from the group consisting of Factor X-activating enzyme and Factor $X_a$.

34. The assay of claim 21 or 22 wherein each of said phospholipid reagents further comprise phosphatidylcholine.

35. The assay of claim 21 or 22, wherein each of said phospholipid reagents comprise 40% phosphatidylethanolamine, 20% phosphatidylserine and 40% phosphatidylcholine.

36. The assay of claim 21, further comprising the steps of:
  (d) conducting a clotting assay by obtaining a first aliquot of a normal patient plasma, providing activated protein C, providing said oxidized phospholipid reagent initiating clotting and measuring the time of clotting to obtain a third clotting time;
  (e) conducting a clotting assay by obtaining a second aliquot of said normal patient plasma, providing activated protein C, providing said non-oxidized phospholipids reagent, initiating clotting and measuring the time of clotting to obtain a fourth clotting time; and
  (f) concluding that if the first clotting time is not as prolonged as the second clotting time, taking into account how much said third clotting time is prolonged over said fourth clotting time, then said patient has a higher propensity for thrombotic disease than a subject with normal plasma.

37. The assay of claim 21 or 22 wherein said phospholipid reagent comprises an effective amount of phosphatidylethanolamine to provide a differential, detectable effect between normal (control) plasma and plasma from patients having a propensity for thrombotic episodes and an effective amount of phosphatidylserine to complement said phosphatidylethanolamine in said clotting assay.

38. The assay of claim 37, wherein said phospholipid reagent further comprises a phospholipid selected from the group consisting of phosphatidyl choline and zwitterionic phospholipids which have no net charge at neutral pH.

39. The assay of claim 21 or 22, wherein said phospholipid reagent comprises from about 10 to about 50% phosphatidylethanolamine and from about 5 to about 50% phosphatidylserine.

40. The assay of claim 39, wherein said phospholipid reagent further comprises a phospholipid selected from the group consisting of phosphatidyl choline and zwitterionic phospholipids which have no net charge at neutral pH.

41. The assay of claim 21 or 22, wherein said phospholipid reagent comprises phosphatidylserine in an amount from about 5 to about 25%.

42. The assay of claim 21 or 22, wherein said phospholipid reagent further comprises a phospholipid selected from the group consisting of phosphatidyl choline and zwitterionic phospholipids which have no net charge at neutral pH.

43. The assay of claim 21 or 22 wherein said phospholipids reagent comprises about 40% PE, about 20% PS and the remainder a phospholipid selected from the group consisting of phosphatidyl choline and zwitterionic phospholipids which have no net charge at neutral pH.

44. The assay of claim 21 or 22, wherein clotting is initiated by addition of an initiator selected from the group consisting of Factor X-activating enzyme and Factor $X_a$.

* * * * *

UNITED STATES PATENT AND TRADEMARK OFFICE
CERTIFICATE OF CORRECTION

PATENT NO. : 7,011,956 B1
APPLICATION NO. : 10/088021
DATED : March 14, 2006
INVENTOR(S) : Naomi L. Esmon and Omid Safa Jamilabadi It is certified that error appears in the above-identified patent and that said Letters Patent is hereby corrected as shown below:

Col. 2, line 6, replace "those" with -- these --
Col. 4, line 25, replace "Paliski" with -- Palinski --
Col. 4, line 56, replace "cloning" with -- clotting --
Col. 7, line 45, replace "(6.25nM)" with -- (6.25mM) --
Col. 8, line 16, replace "66;43-53" with -- 66:43-53 --
Col. 8, line 28, replace "P2-glycoprotein" with -- β2-glycoprotein --
Col. 8, line 43, replace "P2-glycoprotein" with -- β2-glycoprotein --
Col. 11, line 45, replace "sad normal" with -- said normal --
Col. 12, line 47, replace "reagents" with -- reagent --

Signed and Sealed this

Eleventh Day of July, 2006

JON W. DUDAS
*Director of the United States Patent and Trademark Office*